United States Patent [19]
Fuisz

[11] Patent Number: 5,268,110
[45] Date of Patent: Dec. 7, 1993

[54] OIL REMOVING METHOD

[75] Inventor: Richard C. Fuisz, Great Falls, Va.

[73] Assignee: Fuisz Technologies Ltd., Chantilly, Va.

[21] Appl. No.: 936,126

[22] Filed: Aug. 27, 1992

Related U.S. Application Data

[63] Continuation-in-part of Ser. No. 4,053, May 13, 1992, which is a continuation-in-part of Ser. No. 702,068, May 17, 1991.

[51] Int. Cl.$^5$ .................... C02F 1/28; B01D 15/00
[52] U.S. Cl. .................... 210/693; 210/799; 210/924; 210/691; 210/692
[58] Field of Search ............... 210/691, 692, 693, 922, 210/924, 925, 799, DIG. 5

[56] References Cited

U.S. PATENT DOCUMENTS

| | | |
|---|---|---|
| 2,826,169 | 3/1958 | Le Veen . |
| 2,918,404 | 12/1959 | Mende et al. . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,131,428 | 5/1964 | Mika . |
| 3,308,221 | 3/1967 | Opfell . |
| 3,324,061 | 6/1967 | Tanquary et al. . |
| 3,557,717 | 1/1971 | Chivers . |
| 3,595,675 | 7/1971 | Ash et al. . |
| 3,615,671 | 10/1971 | Schoaf . |
| 3,625,214 | 12/1971 | Higuchi . |
| 3,723,134 | 3/1973 | Chivers . |
| 3,762,846 | 10/1973 | Chivers . |
| 3,843,517 | 10/1974 | McKinney et al. ............ 210/922 |
| 3,856,443 | 12/1974 | Salvi . |
| 3,875,300 | 4/1975 | Homm et al. . |
| 3,925,525 | 12/1975 | LaNieve . |
| 3,930,043 | 12/1975 | Warning et al. . |
| 3,951,821 | 4/1976 | Davidson . |
| 3,960,722 | 6/1976 | Tomakawa et al. . |
| 3,967,623 | 7/1976 | Butterworth et al. . |
| 3,992,265 | 11/1976 | Hansen . |
| 4,011,175 | 3/1977 | Preus . |
| 4,070,287 | 1/1978 | Wiegand et al. ............ 210/693 |
| 4,072,658 | 2/1978 | Okamoto et al. . |
| 4,072,794 | 2/1978 | Tomita et al. . |
| 4,090,920 | 5/1978 | Studer, Jr. . |
| 4,136,145 | 1/1979 | Fuchs et al. . |
| 4,153,512 | 5/1979 | Messner et al. . |
| 4,183,984 | 1/1980 | Browers et al. . |
| 4,187,187 | 2/1980 | Turbeville . |
| 4,206,080 | 6/1980 | Sato et al. . |
| 4,293,570 | 10/1981 | Vadasz . |
| 4,303,684 | 12/1981 | Pitchon et al. . |
| 4,332,854 | 6/1982 | Parker ............ 210/924 |
| 4,335,232 | 6/1982 | Irwin . |
| 4,371,516 | 2/1983 | Gregory et al. . |
| 4,376,743 | 3/1983 | Dees . |
| 4,420,400 | 12/1983 | Weitzen ............ 210/925 |

(List continued on next page.)

FOREIGN PATENT DOCUMENTS

| | | |
|---|---|---|
| WO91/18613 | 12/1991 | European Pat. Off. . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |

OTHER PUBLICATIONS

Wayne R. Sorenson, Second Edition Interscience Publishers, *Preparative Methods of Polymer Chemistry*.
Fred W. Billmeyer, Jr., *Polymer Science* Interscience Publishers.
The Merck Index (1989), 11 Ed.

Primary Examiner—Stanley S. Silverman
Assistant Examiner—Cynthia L. Nessler
Attorney, Agent, or Firm—Hoffmann & Baron

[57] ABSTRACT

A method for separating oleaginous material from an aqueous medium is provided. An oil-containing aqueous medium is contacted with an oil-sorbing matrix prepared by subjecting a feedstock to conditions which alter its physical and chemical structure to provide a hydrophobic oil hog. The feedstock includes a hydrophobic matrix having oleaginous-imbibition capability in an oil-hog-altered physical state.

19 Claims, No Drawings

U.S. PATENT DOCUMENTS

| | | |
|---|---|---|
| 4,492,685 | 1/1985 | Keith et al. . |
| 4,496,592 | 1/1985 | Kuwahara et al. . |
| 4,500,546 | 2/1989 | Turbak et al. . |
| 4,502,975 | 3/1985 | Kobayashi et al. ................. 210/922 |
| 4,526,525 | 7/1985 | Oiso et al. . |
| 4,537,877 | 8/1985 | Ericcson ............................ 502/402 |
| 4,560,482 | 12/1985 | Canevari ............................. 210/925 |
| 4,585,797 | 4/1986 | Cioca . |
| 4,619,833 | 10/1986 | Anderson . |
| 4,737,394 | 4/1988 | Zafiroglu ............................ 210/924 |
| 4,758,354 | 7/1988 | O'Mara et al. . |
| 4,793,782 | 12/1988 | Sullivan . |
| 4,822,490 | 4/1989 | Dyadechko et al. ............... 210/922 |
| 4,832,852 | 5/1989 | Wells et al. ......................... 210/691 |
| 4,855,326 | 8/1989 | Fuisz . |
| 4,871,501 | 10/1989 | Sugimoto et al. . |
| 4,873,085 | 10/1989 | Fuisz . |
| 4,874,528 | 10/1989 | Foreman et al. . |
| 4,885,281 | 12/1989 | Hanstein et al. . |
| 4,939,063 | 7/1990 | Tamagawa et al. . |
| 4,981,535 | 1/1991 | Hadermann et al. . |
| 4,987,537 | 12/1990 | Song . |
| 4,997,856 | 3/1991 | Fuisz . |
| 5,000,803 | 3/1991 | Hadermann . |
| 5,011,532 | 4/1991 | Fuisz . |
| 5,028,632 | 7/1991 | Fuisz . |
| 5,034,421 | 7/1991 | Fuisz . |
| 5,039,414 | 8/1991 | Mueller et al. ...................... 210/922 |
| 5,073,387 | 12/1991 | Whistler . |
| 5,082,682 | 1/1992 | Peterson . |
| 5,082,684 | 1/1992 | Fung . |
| 5,084,295 | 1/1992 | Whelan et al. . |
| 5,094,872 | 3/1992 | Furcsik et al. . |
| 5,096,492 | 3/1992 | Fuisz . |

OIL REMOVING METHOD

This application is a continuation-in-part application of PCT application Ser. No. PCT/US92/04053 which was filed May 13, 1992, which in turn is a continuation-in-part of U.S. application Ser. No. 702,068 filed on May 17, 1991. The present invention relates to improvements in oil recovery techniques. In particular, the invention is directed to recovery of oleaginous materials from aqueous-based media and containment of oleaginous materials from aqueous-based media.

BACKGROUND OF THE INVENTION

Over the years, the increased demand for hydrocarbon products has resulted in expanded production, storage and handling of not only crude oils but various distillates. Several activities involved in the production, storage and handling of such products occurs in or near bodies of water. For example, crude oil may be drilled off shore, and transportation of the crude may be carried out by pipeline or ocean-going vessels. As a result of this increased activity, the likelihood of accidental spilling of petroleum-based products into various bodies of water has increased. Such inadvertent spills, can and do occur frequently. Further, on rare occasions, excessive amounts of petroleum-based products or oils can be discharged. These incidences have had well-documented devastating effects on the environment. They have caused long-lasting and even permanent damage to property and the surrounding ecosystem.

In recent years, increased emphasis has been placed on the preservation of the environment. In this regard, efforts have been directed to attending quickly to and containing spills which can be hazardous to the environment. Controlling, neutralizing and recovering contaminating and oily discharges have become an international concern.

Several approaches have been suggested for ameliorating the devastating effects of oil contamination. For example, U.S. Pat. No. 4,011,175 discloses using comminuted demoisturized mixtures containing perlite, clays and fibrous fillers. The comminution is preferably carried out with a hammer mill. The resultant granules are described as loose, fibrous materials which are oleophilic, hydrophobic and floatable on water for selective absorption and stabilization of hydrocarbons in a hydrocarbon-water system.

U.S. Pat. No. 4,072,794 discloses oil adsorbents containing natural fibers such as coconut husk or grass fibers treated with a paraffin wax emulsion and dried. The oil adsorbent is then treated with a latex material and cured. The natural fibers which have been subjected to a combination of treatments with paraffin and latex, are used as oil adsorbents in the form of mats, belts, or lumps.

U.S. Pat. No. 4,070,287 discloses the use of blends of polymeric and cellulosic fibers bound into a web or mat-like structure or retained in a net for removing oils from aqueous systems.

U.S. Pat. No. 3,960,722 oil adsorbents prepared from polyethylene resins and calcium. The mixture is introduced into oil-containing systems as a foam which is preferably shaped into a network of some sort such as a sheet or extruded as a rope.

More recently, U.S. Pat. No. 4,874,528 discloses methods for treating dispersions of oleophilic liquids and water. The methods include well known methods of separation as, for example settling, decantation, centrifugation and flotation.

Additional and various method are still needed for oil recovery. In particular, it is desirable to increase the dispersibility of the adsorbents in the contaminated aqueous systems and to enhance the amounts of oil which can be recovered per unit of sorbent.

It is, therefore, an object of the present invention to provide improved oil separation techniques by improving the dispersal of the sorbents and providing sorbents with increased oil gathering capacity.

Other and further objects of the present invention will be set forth in the following description, and its scope will be pointed out in the appended claims.

SUMMARY OF THE INVENTION

The present invention provides means for separation and recovery of oleaginous substances from aqueous media. The method includes contacting an oleaginous-containing aqueous medium with an oil-sorbing matrix prepared by subjecting a feedstock which includes a hydrophobic material to conditions which alter the physical and/or chemical structure of the feedstock thereby obtaining an oil hog having oil imbibition capability. When the oil-sorbing matrix contacts oleaginous-containing aqueous systems, the oleaginous substances are selectively separated from the aqueous medium. An especially advantageous method includes maintaining a temperature difference of at least 20° F. between the aqueous medium and the melting point of the hydrophobic material.

In one embodiment the oil hog can be made by subjecting a polymeric material to altering conditions such that it becomes oil imbibing after processing while retaining its hydrophobic nature. It has been found that polyethylene can be altered by processing to be both hydrophobic and oil imbibing. In selecting a polymer for use in the present method, it is important to find one which can be processed to an oil-imbibing substance while retaining hydrophobicity. It is believed that olefinic polymers such as polypropylene, polybutylene, et al. may be used effectively as an oil hog.

The process referred to herein includes subjecting a feedstock to temperature and shear to alter its structure. The feedstock can be fed to a spinning head which is heated sufficiently to permit flow of the feedstock through openings in the spinning head and flung outwardly to reform as a solid. Other procedures which create process conditions similar to that describe above are also considered to be part of the present invention.

The oleaginous imbibition capability can also be provided by a materials such as saccharides, biodegradable polymers, cellulosic materials and mixtures thereof. In one embodiment, the saccharide-based materials include sucrose or relatively low dextrose equivalent (D.E.) materials such as maltodextrins. The thermoplastic polymers include materials such as polypropylene, polystyrene and the like. Suitable cellulosic materials include, for example, methyl and ethyl celluloses.

When saccharides are used as the oil-imbibing component, a hydrophobic material can also be selected for its ability to render the saccharide insoluble in water. The hydrophobic material can be selected from a non-limiting list of materials such as vaseline, petroleum jelly, tar, paraffin wax, polyisobutylene, polyethylenes, polypropylenes, styrene butadiene and mixtures thereof.

As a result of the present invention, the difficulties associated with separating oleaginous materials from aqueous systems have been minimized or overcome. The oleaginous-separating matrix allows the artisan to efficiently contact oil-sorbing material with the oleaginous material in the aqueous medium. Moreover, the method and matrix of the present invention allow the artisan to recover up to substantial amounts of oleaginous materials. For example, the oil-sorbing properties of the matrix allow the artisan to recover up to about 20 times its weight of oleaginous material from the aqueous system.

A further embodiment of the present invention includes the use of an entrainment device such as a net can to prevent separation of the oil-imbibing matrix. Separation can occur from mechanical forces acting on matrix. Waves and currents can, for example, be sources of mechanical forces Which act to separate the matrix. The entrainment device simply entraps the matrix, permits oil-imbibition by the matrix, and enables retrieval of the matrix after oleaginous material has been separated from the aqueous medium.

In yet another embodiment, the method is enhanced by adding a gelling agent, such as Elastol ®, which also serves to gel or congeal the oleaginous materials for recovery. The gelling agent provides ar even more efficient recovery from the aqueous system. Substantial time and labor savings are therefore realized.

For a better understanding of the present invention, references made to the following description and its scope will be pointed out in the appended claims.

DETAILED DESCRIPTION OF THE INVENTION

The present invention provides a new and highly efficient technique for separating oleaginous materials from aqueous systems. In this regard, an oil sorbing matrix material is prepared by subjecting a feedstock having a hydrophobic carrier to flash flow conditions thereby obtaining an oil hog of altered physical and/or chemical properties. The oil hog thus obtained has the properties of 1) resisting dissolution in an aqueous medium and 2) imbibing several times its weight of oleaginous material(s). The transformed feedstock is described herein as being in an oil-hog-altered state, which means that the matrix resulting from the process selectively imbibes oil from an aqueous medium.

Oleaginous materials, such as petroleum-based hydrocarbons and/or other organic contaminants are generally immiscible with water and, because of their lower density, float on water. Typical of the liquids immiscible with aqueous systems are the many different types of liquid hydrocarbons. Examples of such materials include crude oil, gasoline, kerosene, light oils, heavy oils, jet fuel, petroleum, asphalt and paraffin crudes, diesel oil, naphtha, certain ketones, aromatic solvents such as benzene, toluene or xylene, terpenes, esters, phenols, certain aldehydes, amides, fatty acids, fatty acid esters, polyorganic compounds and the like and mixtures thereof. For the purpose of describing the present invention, the above-mentioned are hereinafter described as oleaginous materials or oils.

The matrix of the present invention is prepared by subjecting the feedstock, simultaneously either 1) to flash heating and applied physical force, or 2) to flash force and applied heat such that the mixture experiences sufficient internal flow to transform the feedstock into a solid matrix which has a physically and/or chemically altered structure when compared to the pretreated feedstock. The internal flow of the feedstock is at particle or subparticle level. The infrastructure of the material breaks down sufficiently to permit movement of the material at a sub-particle level, and probably at a molecular level. At a molecular level, internal flow contemplates the movement of molecules relative to each other.

Internal flow of material is generally associated with melting point or glass transition point measurements. However, for the purpose of the present invention, it is contemplated that the combined application of heat and external force is sufficient to produce the flow at temperatures below the melting or glass transition point for most compositions. The resultant matrix demonstrates excellent oil-sorption characteristics and is hydrophobic in nature. The temperature at which the feedstock flows is below the temperature at which any material contained in the feedstock degrades.

An apparatus which has been found useful for carrying out the present spinning process is one which was historically used to make cotton candy. The Econo-Floss Machine Model 3017, manufactured by Gold Medal Products Company of Cincinnati, Ohio can be used. It will be appreciated by those skilled in the art from the present description that any apparatus or physical process which provides similar forces and temperature gradient conditions can be used.

The flash flow phenomena of the present invention occurs in not more than one second. Preferably the flow from solid to solid occurs on the order of tenth of seconds, e.g. not more than about 0.4 seconds, and most preferably on the order of milliseconds—certainly not more than 100 milliseconds, i.e., 0.1 second. This unique phenomenon can be produced by relatively high speed distribution of the feedstock material to a spinning element maintained at an elevated temperature under a constant force, such as centrifugal force caused by high speed rotation of a continuous-wall spinning head. One example of a mechanism for producing such as combination is a cotton candy making machine. Variations of such an apparatus are contemplated for use in the present invention. The important aspect is that the flash flow phenomena be induced in a feedstock for rapid transition to a hydrophobic material having an altered structure which is oil imbibing.

Under certain conditions, optimum processibility of the feedstock can be obtained. The apparatus in all instances is to be operated at temperatures and speeds which permit flash flow but do not deteriorate the material undergoing processing. The resulting matrix product can take the form of a particle, flake, floss, fiber, spicule or otherwise generally non-descript aggregate which displays the dispersibility in an oleaginous-bearing aqueous media.

The hydrophobic materials which may be spun with saccharides includes thermoplastic polymers, biodegradable polymers, cellulosic materials, petroleum jelly, vaseline, polyethylene, tar and paraffin or mixtures thereof. In a preferred embodiment, the feedstock may also include agents which enhance separation by gelling and coalescing the oleaginous material. Oleaginous material thus coalesced can be readily separated from the aqueous medium and removed. Polymers such as polyisobutylene or styrene butadiene can be used.

In one particularly preferred embodiment, the gelling agent is polyisobutylene cryogenically ground prior to being added to the feedstock. As contemplated for use herein, the polyisobutylene has an average molecular weight of from about 38,000 to about 6,000,000 and preferably an average molecular weight of at least 3,000,000. Elastol ® is a tradename for such a polyisobutylene. It is used to enhance the viscoelasticity of oil. As a result, Elastol-treated oil can be easily removed from water because it does not disperse or emulsify.

Various materials having oleaginous imbibition capability can also be combined with a hydrophobic material in order to form the matrix of the invention. In one embodiment, the oleaginous imbibition capability is provided by a saccharide-based component. A non-limiting list of materials useful as such component include sugars such as sucrose, lactose, fructose, dextrose, maltose, sorbitol, mannitol and the like. In addition, saccharide-based materials having a lower dextrose equivalents (D.E.) such as corn syrup solids or maltodextrins can be used. In this regard, such materials have a D.E. of less than 40, and preferably within the range of from about 20 to about 40, and alternatively in the range of from about 10 to about 20. Examples of such low D.E. materials are sold under the trademark Maltrin ®, a product of the Grain Processing Corporation of Muscatine, Iowa, or the Hubinger Company under the Dri-Sweet 36 corn syrup solids. Other saccharide-based materials such as polydextrose can also be used. It has been found that maltodextrin flakes which include hydrophobic materials such as paraffin wax make excellent oil spill sorbents when floated on top of an oil spill.

In another aspect of the invention, paraffin wax-bearing maltodextrin flakes can be used to disperse rapidly and uniformly bacteria, microorganisms and enzymes useful as bioremediation agents. In this manner the recovered and/or supernatant oil can also be treated to reduce the deleterious effect on the environment.

Many species of bacteria, fungi and algae have an enzymatic capability to digest petroleum hydrocarbons. The bacteria genera most frequently isolated as hydrocarbon degraders are Pseudomonas, Acinetobacter, Flavobacterium, Brevibacterium, Corynebacterium, Arthrobacter. The fungus genera include Candida, Cladosporium, Trichosporium and Rhodotorula. These bacteria and fungi are present in the environment. Genetically engineered bacteria which have the enzymatic capability of degrading several groups of hydrocarbons can also be used as petroleum biodegraders.

In an alternative aspect of the present invention, thermoplastic polymers can be used to provide both the carrier and the oleaginous imbibition capability. By the term "thermoplastic", it is meant that the polymer softens when exposed to heat and returns to its original condition when cooled to room temperature. Such substances may be of natural origin such as crude rubber and waxes, however, as used herein, the term "thermoplastic" polymers refers generally to synthetic substances. A non-limiting list of such substances include polyvinylchloride, nylons, fluorocarbon-containing polymers, linear polyethylene, polyurethane, polystyrene, polypropylene and certain acrylic resins. A more detailed discussion of new thermoplastic materials and a process for making the same is set forth in co-pending PCT/U.S. application Ser. No. 92/04053, the disclosure of which is incorporated herein by reference.

In yet another aspect of the present invention, the oleaginous-sorbing capability can be a water-soluble cellulosic material. A non-limiting list of such materials includes methyl celluloses, ethyl celluloses, hydroxymethyl and/or hydroxyethyl celluloses, alkali metal salts of carboxymethyl celluloses and the like and mixtures thereof.

Details of the invention have been set forth herein in the form of examples which are described below. The full scope of the invention will be pointed out in the claims which follow the specification.

EXAMPLES

In each of the following examples, the material is subjected to processing in an Econo Floss machine which has been described hereinbefore in this specification. Unless otherwise indicated the temperature of the heating element in the Econo Floss machine was maintained at one of about 284° F. (140.0° C.) at low setting, about 390° F. (198.9° C.) at medium setting, and about 430° F. (221.1° C.) at high setting. Unless otherwise specified, the operating speed of the Econo Floss machine was maintained at about 3600 rpm.

EXAMPLE 1

100 gm of a polyethylene having a molecular weight of 10,000, and bearing the trade name Epolene ® N-10 (from Eastman Chemical Company), was subjected to conditions of temperature and shear sufficient to induce flash flow in the Econo Floss machine. A high quality soft, fluffy floss resulted from the process.

EXAMPLE 2

0.25 grams of polyisobutylene bearing the tradename Elastol ® and 24.75 grams of Epolene ® N-10 were mixed for 5 minutes by using a mortar and pestle assembly so that the Elastol was evenly distributed throughout the Epolene. The unspun material was white and granular. The mixture was then spun under conditions of high temperature and shear in the Econo Floss processing machine. A white spun floss having 1% by weight polyisobutylene was formed. The spun floss also had some chunks. The chunks were picked out and respun. A yield of 80% of the starting material was obtained.

EXAMPLE 3

Two beakers each containing 400 ml of Sears SAE 30 motor oil and 500 ml of Instant Ocean seawater were prepared. 20 grams of the Epolenes floss prepared in accordance with Example 1 was added to one of the beakers and allowed to stand for 30 minutes. 20 grams of 1% polyisobutylene and Epolene ® floss prepared in accordance with Example 2 was added to the other beaker and allowed to stand for 30 minutes. Both oil sorbents soaked most of the oil or almost twenty times their weight. Then, the oil sorbents were allowed to stand overnight. It was noticed that the 1% polyisobutylene/Epolene oil sorbent gelled more than the 100% Epolene oil sorbent.

Thus, the Epolene floss had both described characteristics required of the oil hog—it was both hydrophobic and oil-imbibing. The unique oil-hog-altered structure enabled it to function quite remarkably as a separation means for removing the oleaginous from the water.

The inclusion of the polyisobutyene in Example 2 increased the oil-absorbing efficiency of the matrix. The increased efficiency is believed to be the result of the gelling activity of the polyisobutylene on the oil. Basically, it is thought that the gelling agent enhances the integrity of the target oil. It coalesces the oil and minimizes migration of oil during imbibition. This is an exciting innovation since a vehicle for improving the ability to separate is provided by a target-enhancing agent which can be delivered with the imbibing matrix.

EXAMPLE 4

A new oil sorbent was prepared by mixing 10 grams of vaseline with 45 grams of polyethylene and 45 grams of granulated sucrose. All three ingredients were mixed in a mortar and pestle assembly. The mixture was spun at high temperature under conditions of shear in the Econo Floss processing machine. A yield of 73% of the starting material was obtained. 5 grams of the floss obtained in this manner was placed in 250 grams of motor oil floating on tap water in a beaker. About 90 grams of oil was soaked or 18 times the weight of the oil sorbent.

In Example 4, the hydrophobic aspect of the matrix was provided by polyethylene and vaseline. The oil-imbibing capability was provided by the altered polyethylene and the altered sugar. Both the polyethylene and the sugar were contacted with the oil after conversion to the oil-hog-altered condition. The vaseline assists in retaining the altered sugar in the oil hog during contact with the oil for imbibition. This is a unique feature of the present oil hog since sugar does not normally imbibe oil or any oleaginous at a rate suitable for use in an oil hog.

EXAMPLE 5

A 15 gram sample of vaseline was mixed with 45 grams of sugar, after which 12 grams of polypropylene were added and mixed well. The final mixture was spun at high temperature in the Econo Floss spinner for about 2-4 minutes. A 5 gram ball of the resulting vaseline-containing floss was introduced to a water-containing beaker in which 100 grams of Exxon Super Flo 10W-40 motor oil had been added. After 10 minutes the ball of floss had soaked almost 20 times its weight of motor oil.

As in Example 4, the polypropylene of Example 5 possessed both hydrophobic and oil-imbibing characteristics in the oil-hog-altered state. The altered sugar was oil-imbibing, and the vaseline acted to retain the altered sugar during oil-sorption. The imbibition capability of the oil-hog prepared in accordance with Example 5 enabled it to separate oil in an amount 20 times greater than its weight.

EXAMPLE 6

Another oil sorbent was prepared by mixing 10 grams of tar with 20 grams of vaseline and 200 grams of sugar. The mixture was spun under conditions of high temperature and shear in the Econo Floss processing machine to produce a floss. A 5 gram sample of the floss was added to a solution of seawater containing 50 grams of mineral oil and left over night. The oil floss imbibed the better portion of the mineral oil. Moreover, the soaked mass held together quite well and the tar did not leach out.

The altered floss produce with the unusual combination of feedstock material in Example 6 is quite unique. The oil hog resulting from this combination selectively extracted mineral oil from seawater without unwanted leaching of tar from the floss.

EXAMPLE 7

A 10 gram sample of vaseline was mixed with 50 grams of sugar and spun in the Econo Floss processing machine at high temperature. A 50 gram float of Exxon Super Flo motor oil was placed in a water-containing beaker. A 5 gram sample of the floss obtained in accordance with the invention was added to the motor oil containing beaker and left overnight. The following day 30 grams of 50 gram oil float were recovered, e.g., six times the weight of the oil sorbent. The efficiency of the oil hog prepared in accordance with Example 7 is quite good.

EXAMPLE 8

A mixture of 20 grams of tar and 100 grams of sugar were added to a mixture of 10 grams of vaseline and 100 grams of sugar. The final mixture Was spun in the Econo Floss processing machine at high temperature for 2-4 minutes. A portion of 5 grams of floss obtained from spinning the mixture was added to 50 grams of mineral oil and allowed to sit overnight. The floss performed comparably to the inventive sample obtained in Example 7, e.g., it sorbed many times its weight of mineral oil.

EXAMPLE 9

A portion of 1.5 gram of Elastol ® was mixed with 7.5 grams of vaseline. This mixture was added to 45 grams of sugar and spun in the Econo Floss processing machine at high temperature for 2-4 minutes. 5 grams of the floss thus obtained was added to 50 grams of Exxon Super Flo motor oil floating on water and allowed to sit overnight. The oil hog floss had sorbed 10 times its weight in motor oil.

The increased efficiency obtained when using Elastol ® is believed to be attributable to its gelling capability. The unclaimed oil remained very viscous and cohesive.

EXAMPLE 10

A 20 gram portion of Black & Decker Thermogrip glue from a glue gun was heated in a beaker until the glue melted. The melted glue was then mixed with 100 grams of sugar and then spun under flash flow conditions at a high temperature to form a sturdy floss. A 5 gram sample of the fresh floss was placed in a beaker containing 50 grams of motor oil floating on Instant Ocean sea water. All of the motor oil was adsorbed. Another 5 grams of the fresh floss was placed on 100 grams of motor oil floatng on instant sea water. The floss adsorbed all of the oil or twenty times its weight. This is another example of unexpectedly superior oil-sorbing achieved by the present invention.

EXAMPLE 11

A 10 gram potion of "vaseline" petroleum jelly from Chesebrough-Ponds, Inc. was mixed in a food processor with 10 grams of isotactic polypropylene obtained from Aldrich Chemical Co., Inc. of Milwaukee, Wis. The mixture was mixed for about 4 minutes and then subjected to flash flow in the Econo Floss machine. A fine textured floss was produced.

A quantity of the floss was placed in a beaker containing "Mazola" corn oil and water. The floss preferentially absorbed the oil. In water alone the floss was hydrophobic. There was no apparent dissolution of the floss in either the oil or water.

EXAMPLE 12

A 15 gram potion of "vaseline" petroleum jelly, 45 grams of "Domino" granulated sugar, and 12 grams of polypropylene were placed in a food processor. The composition was mixed for about 5 minutes, then subjected to conditions of flash flow with the Econo Floss machine using the 130 volt heating element at the high setting. A fine hydrophobic floss was produced. When added to tap water this floss floated on the surface. This demonstrates the ability to reproduce a hydrophobic oil hog having oil-imbibing components.

EXAMPLE 13

A 10 gram sample of a paraffin powder made by cryogrinding Paraseal wax was thoroughly mixed with 90 gm. of Maltrin ® 365 (Grain Processing Co.) maltodextrin. The mixture was then spun in an Econo Floss spinner with a 5½ inch diameter head at 140° C. at 3600 r.p.m. Flakes were formed in the spinning process. The flakes were then added to cold water where they floated on the surface. Ten grams of the flakes were placed on a 33° F. oil/seawater mixture. After 3 minutes, the flakes had absorbed over three times their weight of oil and remained floating on the surface after several hours.

The hydrophobicity was provided primarily by the paraffin. The oil-sorbing characteristic was provided primarily by altered maltodextrin. Neither of these components would be capable of exhibiting significant oil-hog characteristics whatsoever in the absence of processing in accordance with the present invention. However, once the feedstock as processed according to the invention, an excellent oil hog matrix was produced.

Thus, while there have been described what are presently believed to be the preferred embodiments of the present invention, those skilled in the art will appreciate that other and further modifications may be made which come within the scope of the invention and it is intended to include all such other modifications and changes as come with the true spirit of the invention.

What is claimed is:

1. A method of separating an oleaginous substance from an aqueous medium, comprising:
contacting an oleaginous-containing aqueous medium with an oil-sorbing matrix including an oil sorbent prepared by subjecting a feedstock comprising a hydrophobic material which has oleaginous-imbibition capability in an altered physical and chemical state to flash flow conditions which alter the physical and chemical structure of said feedstock to provide said altered physical and chemical state, whereby said matrix separates said oleaginous substance from said aqueous medium;
wherein said flash flow conditions comprise simultaneously subjecting said feedstock to conditions of flash heating and applied physical force or flash force and applied heat.

2. The method of claim 1, wherein a temperature difference of at least 20° F. between said aqueous medium and the melting point of said hydrophobic material is maintained during said contacting.

3. The method of claim 1 wherein said feedstock is a polymeric material which imbibes oleaginous substance in said altered state and which is hydrophobic in said altered state.

4. The method of claim 3 wherein said polymeric material is polyethylene.

5. The method of claim 1, wherein said hydrophobic material is selected from the group consisting of petroleum jelly, polyethylene, polypropylene, tar, paraffin wax, styrene butadiene and mixtures thereof.

6. The method of claim 1, wherein said oleaginous imbibition capability is provided by including in said feedstock a material selected from the group consisting of saccharides, thermoplastic polymers, cellulosic materials, biodegradable polymers and mixtures thereof.

7. The method of claim 6, wherein said oleaginous imbibition material is a saccharide selected from the group consisting of glucose, sucrose, lactose, fructose, dextrose, maltose, sorbitol, mannitol, polydextrose, maltodextrins and mixtures thereof.

8. The method of claim 6, wherein said oleaginous imbibition material is a thermoplastic polymer selected from the group consisting of polypropylene, polystyrene, polyethylene, polyvinyl acetate, polyvinyl alcohol, poly (methyl methacrylate), polyacrylic resin, lactide/glycoside copolymer, and combinations thereof.

9. The method of claim 6, wherein said oleaginous imbibition material is a cellulosic material is selected from the group consisting of methyl celluloses, ethyl celluloses, hydroxymethyl celluloses, hydroxyethyl celluloses, alkali metal salts of carboxymethyl celluloses and mixtures thereof.

10. The method according to claim 6, wherein said oleaginous imbibition material is a biodegradable polymers selected from the group consisting of poly (cisisoprene), aliphatic polyesters, polyurethanes, ureaformaldehyde polymers and mixtures thereof.

11. The method according to claim 1 wherein said feedstock further comprises an oleaginous-target enhancer which increases the efficiency of separating said oleaginous from said aqueous medium.

12. The method of claim 11 wherein said enhancer is a gelling agent which inhibits escape of oleaginous material during said contacting.

13. The method according to claim 11, wherein said enhancer is polyisobutylene.

14. The method of claim 13, wherein said polyisobutylene is cryogenically ground.

15. The method of claim 13, wherein said polyisobutylene has an average molecular weight of from about 380,000 to about 6,000,000.

16. The method of claim 15, wherein said polyisobutylene has an average molecular weight of from about 1,000,000 to about 4,000,000.

17. The method of claim 16, wherein said polyisobutylene has an average molecular weight of at least 3,000,000.

18. The method of claim 1, wherein said oleaginous substances are petroleum-based.

19. The method of claim 1, wherein said oil adsorbing matrix further comprises bioremediaton agents.

* * * * *